(12) United States Patent
Keener et al.

(10) Patent No.: US 11,000,045 B2
(45) Date of Patent: May 11, 2021

(54) REACTIVE GAS, REACTIVE GAS GENERATION SYSTEM AND PRODUCT TREATMENT USING REACTIVE GAS

(71) Applicant: NanoGuard Technologies, LLC, St. Louis, MO (US)

(72) Inventors: Kevin M. Keener, Ames, IA (US); Mark A. Hochwalt, Chesterfield, MO (US)

(73) Assignee: NanoGuard Technologies, LLC, St. Louis, MO (US)

( * ) Notice: Subject to any disclaimer, the term of this patent is extended or adjusted under 35 U.S.C. 154(b) by 0 days.

(21) Appl. No.: 16/215,187

(22) Filed: Dec. 10, 2018

(65) Prior Publication Data

US 2019/0159471 A1 May 30, 2019

Related U.S. Application Data

(63) Continuation of application No. 14/921,910, filed on Oct. 23, 2015, now Pat. No. 10,194,672.

(51) Int. Cl.
| | |
|---|---|
| *A23B 9/22* | (2006.01) |
| *A61L 2/20* | (2006.01) |
| *A61L 2/14* | (2006.01) |
| *A61L 9/22* | (2006.01) |

(52) U.S. Cl.
CPC ............... *A23B 9/22* (2013.01); *A61L 2/14* (2013.01); *A61L 2/20* (2013.01); *A61L 2/202* (2013.01); *A23V 2002/00* (2013.01); *A61L 9/22* (2013.01); *A61L 2202/25* (2013.01)

(58) Field of Classification Search
CPC ..... A23B 9/22; A61L 2/20; A61L 2/14; A61L 2/202; A23V 2002/00
See application file for complete search history.

(56) References Cited

U.S. PATENT DOCUMENTS

| | | |
|---|---|---|
| 3,891,561 A | 6/1975 | Lowther |
| 4,524,080 A | 6/1985 | Sugisawa et al. |
| 4,643,876 A | 2/1987 | Jacobs et al. |
| 5,184,046 A | 2/1993 | Campbell |
| 5,482,684 A | 1/1996 | Martens et al. |

(Continued)

FOREIGN PATENT DOCUMENTS

| | | |
|---|---|---|
| CA | 2 685 738 | 5/2010 |
| CA | 3039902 | 6/2019 |

(Continued)

OTHER PUBLICATIONS

Lu et al. https://sfamjournals.onlinelibrary.wiley.com/doi/full/10.1111/jam.12426 Journal of Applied Microbiology,/ vol. 116, Issue 4, Dec. 23, 2013. (Year: 2013).*

(Continued)

*Primary Examiner* — Subbalakshmi Prakash
(74) *Attorney, Agent, or Firm* — Evan Law Group LLC

(57) ABSTRACT

A method of treating a product or surface with a reactive gas, comprises producing the reactive gas by forming a high-voltage cold plasma (HVCP) from a working gas; transporting the reactive gas at least 5 cm away from the HVCP; followed by contacting the product or surface with the reactive gas. The HVCP does not contact the product or surface.

40 Claims, 6 Drawing Sheets

(56) References Cited

U.S. PATENT DOCUMENTS

| | | |
|---|---|---|
| 5,656,238 A | 8/1997 | Spencer et al. |
| 5,896,587 A | 4/1999 | Sorensen |
| 6,007,770 A | 12/1999 | Peiper et al. |
| 6,093,432 A | 7/2000 | Mittal et al. |
| 6,096,564 A | 8/2000 | Denes et al. |
| 6,171,450 B1 | 1/2001 | Behnisch et al. |
| 6,403,029 B1 | 6/2002 | Schmidt |
| 6,406,759 B1 * | 6/2002 | Roth .................... A61L 2/14 134/1.1 |
| 6,543,460 B1 | 4/2003 | Denes et al. |
| 6,638,475 B1 | 10/2003 | Lagunas-Solar et al. |
| 6,667,007 B1 | 12/2003 | Schmidt |
| 6,991,768 B2 | 1/2006 | Keras et al. |
| 7,101,518 B1 | 9/2006 | Ko |
| 8,097,217 B2 | 1/2012 | Song |
| 8,343,422 B2 | 1/2013 | Sato et al. |
| 8,372,460 B2 | 2/2013 | Meyers et al. |
| 8,475,712 B2 | 7/2013 | Henriksson |
| 8,475,723 B2 | 7/2013 | Keras |
| 8,545,764 B2 | 10/2013 | Gesche |
| 8,551,546 B2 | 10/2013 | Rasanayagam et al. |
| 8,557,187 B2 | 10/2013 | Ehlbeck et al. |
| 8,641,977 B2 | 2/2014 | Snowball |
| 8,771,595 B2 | 7/2014 | Paskalov |
| 8,834,803 B2 | 9/2014 | Sunderland |
| 8,865,085 B2 | 10/2014 | Nam et al. |
| 8,871,145 B2 | 10/2014 | Paskalov |
| 8,920,740 B2 | 12/2014 | Yang et al. |
| 8,961,894 B2 | 2/2015 | Keener et al. |
| 8,980,190 B2 | 3/2015 | Diver et al. |
| 9,067,788 B1 | 6/2015 | Spielman et al. |
| 9,114,373 B2 | 8/2015 | Misawa et al. |
| 9,220,162 B2 | 12/2015 | Takenoshita et al. |
| 9,295,280 B2 | 3/2016 | Jacofsky et al. |
| 9,363,880 B2 | 6/2016 | Keener et al. |
| 9,408,930 B2 | 8/2016 | Keener et al. |
| 9,539,352 B2 | 1/2017 | Keener et al. |
| 9,597,422 B2 | 3/2017 | Snowball |
| 10,194,672 B2 | 2/2019 | Keener et al. |
| 2002/0129902 A1 | 9/2002 | Babayan et al. |
| 2002/0153241 A1 | 10/2002 | Niv et al. |
| 2002/0175068 A1 | 11/2002 | Hammerstrom et al. |
| 2002/0182101 A1 | 12/2002 | Koulik et al. |
| 2003/0026877 A1 | 2/2003 | Ruan et al. |
| 2003/0030374 A1 | 2/2003 | Pai |
| 2003/0039726 A1 | 2/2003 | Yuan |
| 2003/0164285 A1 | 9/2003 | Korenev |
| 2003/0168009 A1 | 9/2003 | Denes |
| 2004/0001773 A1 | 1/2004 | Schmidt |
| 2004/0037736 A1 | 2/2004 | Perruchot et al. |
| 2004/0047762 A1 | 3/2004 | Masaoka et al. |
| 2004/0050682 A1 | 3/2004 | Paskalov et al. |
| 2004/0076543 A1 | 4/2004 | Sokolowski et al. |
| 2004/0131496 A1 | 7/2004 | Goetzelmann et al. |
| 2004/0141278 A1 | 7/2004 | Grosse et al. |
| 2004/0208804 A1 | 10/2004 | Hall et al. |
| 2004/0216845 A1 | 11/2004 | Golkowski |
| 2004/0250688 A1 | 12/2004 | Farkas et al. |
| 2005/0019209 A1 | 1/2005 | Burger et al. |
| 2005/0056596 A1 | 3/2005 | Paskalov et al. |
| 2005/0109739 A1 | 5/2005 | Destrez et al. |
| 2005/0127843 A1 | 6/2005 | Koulik et al. |
| 2005/0196315 A1 | 9/2005 | Babko-Malyi et al. |
| 2005/0274122 A1 | 12/2005 | Chang et al. |
| 2006/0027539 A1 | 2/2006 | Golkowski |
| 2006/0060464 A1 | 3/2006 | Chang |
| 2006/0137212 A1 | 6/2006 | Nomine |
| 2006/0251550 A1 | 11/2006 | Keras |
| 2007/0020159 A1 | 1/2007 | Tsui |
| 2007/0104610 A1 | 5/2007 | Houston et al. |
| 2007/0261555 A1 | 11/2007 | Aubert |
| 2007/0270833 A1 | 11/2007 | Bonutti et al. |
| 2008/0006536 A1 | 1/2008 | Cuomo et al. |
| 2008/0063559 A1 | 3/2008 | Alexander et al. |
| 2008/0099406 A1 | 5/2008 | Ruan et al. |
| 2008/0173621 A1 | 7/2008 | Kuo |
| 2008/0193330 A1 | 8/2008 | Hotta et al. |
| 2008/0258648 A1 | 10/2008 | Bleukx et al. |
| 2008/0260578 A1 | 10/2008 | Engemann et al. |
| 2008/0292497 A1 | 11/2008 | Vangeneugden et al. |
| 2008/0314243 A1 | 12/2008 | Chan et al. |
| 2009/0121637 A1 | 5/2009 | Laroussi |
| 2009/0159461 A1 | 6/2009 | McCutchen et al. |
| 2009/0274592 A1 | 11/2009 | Bergeron |
| 2009/0288559 A1 | 11/2009 | Kuo |
| 2009/0297409 A1 | 12/2009 | Buchanan et al. |
| 2009/0304562 A1 | 12/2009 | Hayashi et al. |
| 2010/0006121 A1 | 1/2010 | Baxter et al. |
| 2010/0032285 A1 | 2/2010 | Thomas et al. |
| 2010/0119670 A1 | 5/2010 | Mazzariello |
| 2010/0206232 A1 | 8/2010 | Duclos et al. |
| 2010/0209293 A1 | 8/2010 | Ikawa et al. |
| 2010/0304146 A1 | 12/2010 | Krebs et al. |
| 2011/0014330 A1 | 1/2011 | Meyers et al. |
| 2011/0115415 A1 | 5/2011 | Hong |
| 2011/0116967 A1 | 5/2011 | Roy et al. |
| 2011/0251604 A1 | 10/2011 | Staack et al. |
| 2011/0268850 A1 | 11/2011 | Rasanayagam et al. |
| 2012/0000782 A1 | 1/2012 | Hong |
| 2012/0093687 A1 | 4/2012 | Snowball |
| 2012/0156093 A1 | 6/2012 | Kitano |
| 2012/0156340 A1 | 6/2012 | Rasanayagam et al. |
| 2012/0156341 A1 | 6/2012 | Rasanayagam et al. |
| 2012/0183437 A1 | 7/2012 | Keener et al. |
| 2012/0213664 A1 | 8/2012 | Diver et al. |
| 2013/0053761 A1 | 2/2013 | Morfill et al. |
| 2013/0104742 A1 | 5/2013 | Deo et al. |
| 2013/0105025 A1 | 5/2013 | Fehr et al. |
| 2013/0164173 A1 | 6/2013 | Norris |
| 2013/0189156 A1 | 7/2013 | Keener et al. |
| 2013/0196099 A1 | 8/2013 | Sakamoto et al. |
| 2013/0319460 A1 | 12/2013 | Schneider et al. |
| 2013/0345620 A1 | 12/2013 | Zemel |
| 2014/0044595 A1 | 2/2014 | Keener et al. |
| 2015/0150297 A1 | 6/2015 | Kim et al. |
| 2015/0273094 A1 | 10/2015 | Keener et al. |
| 2015/0327430 A1 | 11/2015 | Dong et al. |
| 2015/0327562 A1 | 11/2015 | Zwijack |
| 2015/0342397 A1 | 12/2015 | Deo et al. |
| 2015/0373923 A1 | 12/2015 | Ferrell et al. |
| 2016/0262410 A1 | 9/2016 | Hoefnagels |
| 2017/0000167 A1 | 1/2017 | Corrigan |
| 2017/0112157 A1 | 4/2017 | Keener et al. |
| 2017/0133205 A1 | 5/2017 | Ehlbeck et al. |

FOREIGN PATENT DOCUMENTS

| | | |
|---|---|---|
| CN | 201610939647.X | 2/2019 |
| CN | 201610939647.X | 8/2019 |
| DE | 10 2014 107805 | 1/2015 |
| EP | 1 884 248 | 2/2008 |
| EP | 2 374 753 | 10/2011 |
| EP | 16788620.9 | 1/2018 |
| EP | 3 383 144 | 3/2018 |
| EP | 16788620.9 | 4/2018 |
| EP | 16788620.9 | 9/2018 |
| EP | 16788620.9 | 2/2019 |
| EP | 19155626.5 | 9/2019 |
| EP | 19155626.5 | 2/2020 |
| IN | 201827013136 | 7/2019 |
| JP | 2018-520174 | 7/2019 |
| KR | 10-2018-7012556 | 9/2019 |
| KR | 10-2018-7012556 | 2/2020 |
| MX | MX/a/2018/004893 | 4/2019 |
| MX | MX/a/2018/004893 | 9/2019 |
| RU | 2102084 | 1/1998 |
| RU | 2199349 | 2/2003 |
| RU | 2254143 | 6/2005 |
| RU | 2018118775 | 4/2020 |
| WO | 1997/18343 | 5/1997 |
| WO | 1997/022369 | 6/1997 |
| WO | 1998/51608 | 11/1998 |
| WO | 1998/51609 | 11/1998 |
| WO | 2002/022447 | 4/2000 |

(56) References Cited

FOREIGN PATENT DOCUMENTS

| | | |
|---|---|---|
| WO | 2000/054819 | 9/2000 |
| WO | 2002/078749 | 10/2002 |
| WO | 2006/004399 | 1/2006 |
| WO | 2007/067924 | 6/2007 |
| WO | 2007/124910 | 11/2007 |
| WO | 2007/124945 | 11/2007 |
| WO | 2008/072170 | 6/2008 |
| WO | 2008/096292 | 8/2008 |
| WO | 2008/126068 | 10/2008 |
| WO | 2008/127135 | 10/2008 |
| WO | 2008/144499 | 11/2008 |
| WO | 2009/040130 | 4/2009 |
| WO | 2009/041861 | 4/2009 |
| WO | 2009/098662 | 8/2009 |
| WO | 2011/116984 | 9/2011 |
| WO | 2011/123512 | 10/2011 |
| WO | 2012/038669 | 3/2012 |
| WO | 2012/079858 | 6/2012 |
| WO | 2012/097987 | 7/2012 |
| WO | 2012/112042 | 8/2012 |
| WO | 2012/113568 | 8/2012 |
| WO | 2012/125435 | 9/2012 |
| WO | 2012/130197 | 10/2012 |
| WO | 2013/076102 | 5/2013 |
| WO | 2013/076458 | 5/2013 |
| WO | 2014/135254 | 9/2014 |
| WO | 2014/152169 | 9/2014 |
| WO | 2015/091221 | 6/2015 |
| WO | 2016/007000 | 1/2016 |
| WO | 2016/140447 | 9/2016 |
| WO | 2017/019621 | 2/2017 |
| WO | 2017/070240 | 4/2017 |
| WO | 2018/045378 | 3/2018 |

OTHER PUBLICATIONS

Lopez et al., Frontiers in Microbiology | www.frontiersin.org Apr. 2019 Article 622 | vol. 10 | pp. 1-21 (Year: 2019).*
Ma, H. et al., "Non-thermal pasteurization of liquid foods using non-thermal plasma", Transactions of the CSAE, vol. 18, No. 5, pp. 155-159, (2002).
Li, Y. et al., "Degradation of aflatoxin $B_1$ in agricultural products by low temperature radio frequency plasma", Science and Technology of Cereals, Oils and Foods, vol. 22.5, pp. 1-11, (2014).
International Search Report dated Jan. 25, 2017 for PCT application No. PCT/US2016/057753, 12 pages.
Connolly, J. et al., "Characterization and antimicrobial efficacy against *E. coli* of a helium/air plasma at atmospheric pressure created in a plastic package", Journal of Physics D: Applied Physics, vol. 46, No. 3, pp. 1-12, (2013).
Misra, N.N. et al., "In-package atmospheric pressure cold plasma treatment of cherry tomatoes", Journal of Bioscience and Bioengineering, vol. 118, No. 2, pp. 177-182, (2014).
Chiper, A.S. et al., "Atmospheric pressure plasma produced inside a closed package by a dielectric barrier discharge in $Ar/CO_2$ for bacterial inactivation of biological samples", Plasma Sources Science and Technology, vol. 20, No. 2, pp. 1-10, (2011).
Kolb, J.F. et al., "Cold atmospheric pressure air plasma jet for medical applications", Applied Physics Letters, vol. 92, pp. 241501-1-241501-3, (2008).
Winter, J. et al., "Aspects of UV-absorption spectroscopy on ozone in effluents of plasma jets operated in air", Journal of Physics D: Applied Physics, vol. 45, pp. 1-7, (2012).
Katsonis, K. et al., "Global modeling of $N_2O$ discharges: Rate coefficients and comparison with ICP and glow discharges results", International Journal of Aerospace Engineering, vol. 2013, pp. 1-25. (2013).
"Aflatoxin", Wikipedia, pp. 1-5, found at https://en.wikipedia.org/wiki/Aflatoxin, printed on Jul. 10, 2015.
Lunov, O. et al., "Cell death induced by ozone and various non-thermal plasmas: therapeutic perspectives and limitations", Scientific Reports, vol. 4, pp. 1-11, (2014).

"Volt", Wikipedia, pp. 1-4, found at https://en.wikipedia.org/wiki/Volt, Printed on Jul. 10, 2015.
Moiseev, T. et al., "Post-discharge gas composition of a large-gap DBD in humid air by UV-Vis absorption spectroscopy", Plasma Sources Science and Technology, vol. 23, pp. 1-13, (2014).
"Endospore", Wikipedia, pp. 1-6, found at https://en.wikipedia.org/wiki/Endospore, Printed on Sep. 10, 2017.
Trombete, FM. et al., "Efficacy of ozone treatment on mycotoxins and fungal reduction in artificially contaminated soft wheat grains", Journal of Food Processing and Preservation, vol. 41, No. 3, (2017). Abstract Only.
McKenzie, K.S. et al., "Oxidative degradation and detoxification of mycotoxins using a novel source of ozone", Food and Chemial Toxicology, vol. 35, No. 8, pp. 807-820, (1997). Abstract Only.
Wang L. et al., "Effect of ozone treatment on deoxynivalenol and wheat quality", PLoS One, vol. 11, No. 1, pp. 1-13, (2016).
McDonougha, M.X. et al., "Ozone application in a modified screw conveyor to treat grain for insect pests, fungal contaminants, and mycotoxins", Journal of Stored Products Research, vol. 47, No. 3, pp. 249-254, (2011). Abstract Only.
Tiwari, B.K. et al., "Application of ozone in grain processing", Journal of Cereal Science, vol. 51, issue 3, pp. 248-255, (2010). Abstract Only.
Guzel-Seydima, Z.B. et al., "Use of ozone in the food industry", LWT—Food Science and Technology, vol. 37, No. 4, pp. 453-460, (2004).
"Listeria monocytogenes", Wikipedia, pp. 1-7, found at https://en.wikipedia.org/wiki/Listeria_monocytogenes, printed on Jul. 10, 2015.
"Bacillus atrophaeus", Wikipedia, pp. 1-2, found at https://en.wikipedia.org/wiki/Bacillus_atrophaeus, printed on Jul. 10, 2015.
"*Salmonella enterica*", Wikipedia, pp. 1-3, found at https://en.wikipedia.org/wiki/Salmonella_enterica, printed on Jul. 10, 2015.
"Clostridium botulinum", Wikipedia, pp. 1-6, found at https://en.wikipedia.org/wiki/Clostridium_botulinum, printed on Jul. 10, 2015.
"Sterilization (microbiology)", Wikipedia, pp. 1-10, found at https://en.wikipedia.org/wiki/Sterilization_(microbiology), printed on Jul. 10, 2015.
Food and Drug Administration, "Guidance for industry for the submission documentation for sterilization process validation in applications for human and veterinary drug products", Office of Training and Communication Division of Drug Information, CDER, FDA, pp. 1-18, (1994).
Chaven, S. et al., "Food safety systems for low-acid, aseptic beverages", Food Safety Magazine, pp. 1-6, found at www.foodsafetymagazine.com/magazine-archive1/junejuly-2012/food-safety-systems-for-low-acid-aseptic-beverages/, (2012).
US Food and Drug Administration, "Guidance for Industry: Juice HACCP hazards and controls guidance first edition: Final guidance", pp. 1-67 (2004).
Lopez, J.L., "Dielectric barrier discharge, ozone generation, and their applications", Complex Plasmas Summer Institute, pp. 1-93, (2008).
Pankaj, S.K, et al., "Degradation kinetics or organic dyes in water by high voltage atmospheric air and modified air cold plasma", Water Science & Technology, pp. 1-8, (2017).
Pankaj, S.K. et al., "Effect of high voltage atmospheric cold plasma on white grape juice quaiity", Journal of the Science of Food and Agriculture, vol. 97, pp. 4016-4021, (2017).
Yepez, X.V. et al., "High-voltage atmospheric cold plasma (HVACP) hydrogenation of soybean oil without trans-fatty acids", Innovative Food Science and Emerging Technologies, vol. 38, pp. 169-174, (2016).
Wan, Z. et al., "High voltage atmospheric cold plasma treatment of refrigerated chicken eggs for control of *Salmonella enteritidis* contamination on egg shell", LWT—Food Science and Technology, vol. 76, pp. 124-130, (2017).
Xu, L. et al., "Microbial inactivation and quality changes in orange juice treated by high voltage atmospheric cold plasma", Food Bioprocess Technalbgy, vol. 10, pp. 1778-1791, (2017).
McClurkin-Moore, J.D. et al., "The effect of high-voltage atmospheric cold plasma treatment on the shelf-life of distillers wet grains", Food Bioprocess Technology, vol. 10, 1431-1440, (2017).

(56) References Cited

OTHER PUBLICATIONS

Pankaj, S.K. et al., "Cold plasma: background, applications and current trends", Current Opinion in Food Science, vol. 16, pp. 49-52, (2017).
Shi, H. et al., "Reduction of aflatoxin in corn by high voltage atmospheric cold plasma", Food Bioprocess Technology, vol. 10, pp. 1042-1052, (2017).
Misra, N.N. et al., "The effects of nonthermal plasma on chemical quality of strawberries", Postharvest Biology and Technology, vol. 110, pp. 197-202, (2015).
Hojnik, N. et al., "Mycotoxin decontamination of food: Cold atmospheric pressure plasma versus "classic" decontamination", Toxins, vol. 9, No. 151, pp. 1-19, (2017).
Siciliano, I. et al., "Use of cold atmospheric plasma to detoxify hazelnuts from aflatoxins", Toxins, vol. 8, No. 125, pp. 1-10, (2016).
Chen, Y., "High voltage atmospheric cold plasma treatment of refrigerated chicken eggs for control of *Salmonella enteritidis* on external surfaces", Purdue University, Theses and Dissertations, pp. 1-209, (2014).
Morfill, G.E. et al., "Nosocomial infections—a new approach towards preventive medicine using plasmas", New Journal of Physics, vol. 11, 115019, pp. 1-10, (2009).
Extended European Search Report dated Feb. 25, 2020 for European application No. 19155626.5, 8 pages.
"Ozone effects on pathogens", Ozone Solutions, 5 pages, downloaded on Mar. 13, 2020, found at www.ozonesolutions.com/blog/ozone-effects-on-pathogens-bc5a25/.
"Ozone as a disinfectant to destroy pathogens, like the coronavirus", Ozone Solutions, 2 pages, downloaded on Mar. 13, 2020, found at www.ozonesolutions.com/blog/ozone-as-a-disinfectant-to-destroy-pathogens-like-the-coronavirus/.
Foarde, K. et al., "Ozone antimicrobial efficacy", U.S. Environmental Protection Agency, National Risk Management Research Laboratory, pp. 1-13, (2007).
Apr. 7, 2020, U.S. Appl. No. 16/442,380.
Aug. 21, 2020, U.S. Appl. No. 16/442,380.
U.S. Appl. No. 17/017,517, filed Sep. 10, 2020.
Pradeep, P. et al., "Non-thermal plasmas (NTPs) for inactivation of viruses in abiotic environment", Research Journal of Biotechnology, vol. 11, No. 6, pp. 91-96, (2016).
Wu, Y. et al., "MS2 virus inactivation by atmospheric-pressure cold plasma using different gas carriers and power levels", Applied and Environmental Microbiology, vol. 81, No. 3, pp. 996-1002, (2015).
Yasuda, H. et al., "Biological evaluation of DNA damage in bacteriophages inactivated by atmospheric pressure cold plasma", Plasma Processes and Polymers, vol. 7, pp. 301-308, (2010).
Alshraiedeh, N.H. et al., "Atmospheric pressure, nonthermal plasma inactivation of MS2 bacteriophage: effect of oxygen concentration on virucidal activity", Journal of Applied Microbiology, vol. 115, pp. 1420-1426, (2013).
Bae, S.C. et al., "Inactivation of murine norovirus-1 and hepatitis A virus on fresh meats by atmospheric pressure jets", Food Research International, vol. 76, pp. 342-347, (2015).
Cowling, B.J. et al., "Aerosol transmission is an important mode of influenza A virus spread", Nature Communications, vol. 4, 1935, pp. 1-6, (2013).
Kuzmanovic, D.A. et al., "Bacteriophage MS2: Molecular weight and spatial distribution of the protein and RNA components by small-angle neutron scattering and virus counting", Structure, vol. 11, pp. 1339-1348, (2003).
Wolf, C. et al., "Proxies to monitor the inactivation of viruses by ozone in surface water and wastewater effluent", Water Research, vol. 166, (2019).
Brie, A. et al., "Inactivation of murine norovirus and hepatitis A virus on fresh raspberries by gaseous ozone treatment", Food Microbiology, vol. 70, pp. 1-6, (2018).
Hudson, J.B. et al., "Development of a practical method for using ozone gas as a virus decontaminating agent", Ozone: Science & Engineering, vol. 31, No. 3, pp. 216-223, (2009).
Muller, J.A. et al., "Development of a high-throughput colorimetric Zika virus Infection Assay", Medical Microbiology and Immunology, vol. 206, issue 2, pp. 175-185, (2017).
World Health Organization, "Zika virus Situation Report—Feb. 5, 2016", 6 pages, (2016).
Rasmussen, S.A. et al., "Zika virus and birth defects-reviewing the evidence for causality", The New England Journal of Medicine, pp. 1-7, (2016).
Muller, J.A. et al., "Inactivation and environmental stability of Zika virus", Emerging Infectious Diseases, vol. 22, No. 9, pp. 1685-1687, (2016).
Aubry, M. et al., "Inactivation of Zika virus in plasma with amotosalen and ultraviolet A illumination", Transfusion, vol. 56, pp. 33-40, (2016).
Butot, S. et al., "Procedure for rapid concentration and detection of enteric viruses from berries and vegetables", Applied and Environmental Microbiology, vol. 73, No. 1, pp. 186-192, (2007).
Woolston, J. et al., "Bacteriophage lytic for salmonella rapidly reduce salmonella contamination on glass and stainless-steel surfaces", Bacteriophage, vol. 3, issue 3, pp. e25697-1-.e25697-6, (2013).
Carey-Smith, G.V. et al., "Isolation and characterization of bacteriophages infecting *Salmonella* spp.", FEMS Microbiology Letters, vol. 258, pp. 182-186, (2006).
Soffer, N. et al., "Bacteriophages safely reduce *Salmonella* contamination in pet food and raw pet food ingredients", Bacteriophage, vol. 6, No. 3, pp. e1220347-1-e1220347-8, (2016).
Shin, H. et al., "Receptor diversity and host interaction of bacteriophages infecting *Salmonella enterica* serovar typhimurium", Plos One, vol. 7, issue 8, pp. e43392-1-e43392-11, (2012).
"Influenza type A viruses—Avian influenza (Flu)", Centers for Disease Control and Prevention, 2 pages, found at www.cdc.gov/flu/avianflu/influenza-a-virus-subtypes.htm, (2020).
Dow Corning, Product Information, "Dow Corning® 3-4207 Dielectric Tough Gel", 3 pages, (2017).
Cock, I. et al., "A modified MS2 bacteriophage plaque reduction assay for the rapid screening of antiviral plant extracts", Pharmacognosy Research, vol. 2, issue 4, pp. 221-228, (2010).
ACL Inc., Product Information, "8690 Staticide Acrylic Conformal Coating", 1 page, (2016).
Corning Gorilla Glass, Product Information, "Corning Gorilla Glass 3", 2 pages, (2016).
ResinLab, an Ellsworth Adhesives Company, Product Information, "Technical Data Sheet EP750 Clear", 3 pages, (2016).
ResinLab, an Ellsworth Adhesives Company, "Safety Data Sheet for EP750 Clear A", pp. 1-13, (2015).
ResinLab, an Ellsworth Adhesives Company, "Safety Data Sheet for EP750 Clear B", pp. 1-9, (2015).
Acculam Laminated Thermoset Plastic, Product Data Sheet, "Acculam® Epoxyglas G10, FR4", 1 page, (2017).
Encon2.3 Fact Sheet, "Improving energy efficiency in grain drying", 5 pages, (2012).
Biomin, "World Mycotoxin Survey, The global threat", 5 pages, (2019).
SciFinder Search Report on "Inactivation of Viruses using Ozone", pp. 1-14, generated on Feb. 10, 2020.
EPA, "Guidance to Registrants: Process for making claims against emerging viral pathogens not on EPA-registered disinfectant labels", Environmental Protection Agency, pp. 1-8, (2016).
Oct. 15, 2020, U.S. Appl. No. 15,442,380.
International Search Report dated Oct. 27, 2020 for PCT application No. PCT/US2020/036833, 12 pages.
Jul. 11, 2017, U.S. Appl. No. 14/921,910.
Aug. 30, 2017, U.S. Appl. No. 14/921,910.
Oct. 18, 2017, U.S. Appl. No. 14/921,920.
Sep. 28, 2018, U.S. Appl. No. 14/921,910.

\* cited by examiner

REACTIVE GAS, REACTIVE GAS GENERATION SYSTEM AND PRODUCT TREATMENT USING REACTIVE GAS

BACKGROUND

Biological decontamination and sterilization have a broad array of applications including medical equipment and device sterilization, food production and preservation, and preparation of consumer goods. Chemicals, heat, high-energy electron beams, and X-ray or gamma-ray irradiation systems are presently used for sterilization. Each of these systems has trade-offs due to the cost, efficiency, immobility, electric power requirements, toxic waste, personal hazard and the time required for sterilization or decontamination.

Plasmas have been used for decontamination and sterilization. Plasma, a fourth state of matter distinguished from gas, liquid and solid, may be produced through electrical discharge, for example electrical discharge through a gas. Although all plasmas contain electrons, ions and neutral species, they will have different properties depending on the composition of the gas used to prepare the plasma, as well as the electrical and structural configuration of the device used to produce the plasma.

One type of plasma is high-voltage cold plasma (HVCP), which may be prepared using dielectric barrier discharge (DBD) systems. HVCP may be prepared using non-equilibrium breakdown of a gas, using voltages preferably of 30 kV to 500 kV, typically at a frequency of 50 or 60 Hz with a DBD system. HVCP has not been studies as well as other types of plasmas, such as thermal plasma or RF plasmas. Consequently, there is presently no theory which explains the properties of these plasmas, nor the various excited and reactive species produced in such plasma. Over the last decade experimental examination of HVCP has been carried out to study this plasma.

Direct exposure of materials to HVCP has been studied. Of particular relevance are the studies exposing biological products and contaminants to HVCP, where the biological products are sealed inside packages and the HVCP is produced inside the package. In such studies, packaged foods such as produce and other materials were sterilized in a short period of time. The product inside the packages comes into direct contact with the plasma. Since the packages are sealed, reactive gas produced in the plasma remains in contact with the product indefinitely, is not diluted or dispersed, and the packaged product is protected from recontamination, dramatically extending the shelf life of the products, such as fruits and vegetables. See, for example, U.S. Pat. Pub., Pub. Nos. 2013/0189156 and 2014/0044595, both to Keener et al.

SUMMARY

In a first aspect, the present invention is a method of treating a product with a reactive gas, comprising producing the reactive gas by forming a high-voltage cold plasma (HVCP) from a working gas; transporting the reactive gas at least 5 cm away from the HVCP; followed by contacting the product with the reactive gas. The HVCP does not contact the product.

In a second aspect, the present invention is a method of reducing mycotoxins on grain, comprising producing a reactive gas by forming a high-voltage cold plasma (HVCP) from a working gas; transporting the reactive gas at least 3 meters away from the HVCP; followed by contacting the grain with the reactive gas.

In a third aspect, the present invention is a method of medically sterilizing a surface, comprising producing the reactive gas by forming a high-voltage cold plasma (HVCP) from a working gas; and contacting the surface with the reactive gas. The HVCP does not contact the surface, and the surface is the surface of an enclosed space, or equipment in an enclosed space, where the enclosed space has a volume of at least 8 cubic meters.

In a fourth aspect, the present invention is a method of treating a product or surface with a reactive gas, comprising providing a container having stored reactive gas produced by forming a high-voltage cold plasma (HVCP) from a working gas; and contacting the product or surface with the reactive gas. The reactive gas comprises at least one reactive or excited species other than ozone.

In a fifth aspect, the present invention is a system for treating a product or surface with a reactive gas, comprising (1) A dielectric barrier discharge (DBD) system, and (2) a treatment chamber, fluidly connected to the DBD system. The treatment chamber has a volume of at least 1 cubic meter.

Definitions

All current described herein is alternating current, specified as volts (V) and kilovolts (kV) root mean squared (RMS). Percent (%) gas compositions are volume percents.

A cold plasma refers to plasma which has a temperature of at most 40° C. above the temperature of the gas used to prepare the plasma (that is, the working gas), more preferably a temperature of at most 20° C. above the temperature of the gas used to prepare the plasma.

High-voltage cold plasma (HVCP) means a cold plasma prepared using a dielectric barrier discharge (DBD) system, using voltages of at most 500 kV, with a frequency at most to 1000 Hz, prepared from a gas having a pressure of 10 to 50000 Torr, such as 760 Torr (atmospheric pressure). HVCP is not a thermal plasma, is not a microwave plasma and is not a radio frequency (RF) plasma. HVCP plasmas are prepared under non-equilibrium breakdown conditions.

Reactive gas means the gas produced by an HVCP, including excited and chemically reactive species, but not those species which dissipate in 0.2 seconds or less. The composition of a reactive gas will change over time as excited species dissipate and chemical reactions within the reactive gas take place. Reactive gas is the gas that may be moved away from the DBD system that is producing an HVCP. A reactive species or excited species is considered to be present in a reactive gas if it can be detected using spectroscopy.

Dielectric barrier discharge (DBD), or a DBD system, means a system having at least two electrodes separated by a dielectric barrier, and may have more electrodes, where a dielectric barrier is present between each electrode, to prevent charge generated in the gas by a discharge from reaching an electrode. The shortest distance between adjacent electrodes in a DBD system is preferably at most 30 cm (or 12 inches), and preferably is at least 0.5 cm (or 0.25 inches). Preferably, DBD systems are configures to operate under conditions to produce an HVCP. Examples of DBD systems are illustrated in FIGS. 1A, 1B, 1C, 1D, 1E and 1F; preferably, the electrodes are spaced apart with a gap or plenum directly between the electrodes as illustrated in FIGS. 1A, 1B, 1C and 1F.

Working gas and working gas mixture refers to the gas which is used to form a plasma.

Package means a container having a volume of at most 6 gallons (or 22.7 liters).

Sealed or substantially sealed means that the gases inside the package or container remains inside and not flow or diffuse out of the package or container for at least 24 hours, if left undisturbed.

Sterilizing, or sterilized means medical sterilization or medically sterilized, which means subjecting (or having been subjected) to a treatment sufficient to reduce the number of viable *Bacillus atrophaeus* spores on or in a product or surface to at most $1 \times 10^{-6}$ of the amount present prior to treatment, if such spores had been present.

Canning sterilizing or canning sterilized, means subjecting (or having been subjected) to a treatment sufficient to reduce the number of viable *Clostridium botulinum* spores on or in a product or surface to at most $1 \times 10^{-12}$ of the amount present prior to treatment, if such spores had been present.

*E. coli* pasteurized means subjecting (or having been subjected) to a treatment sufficient to reduce the number of viable *Escherichia coli* O157:H7 on or in a product or surface to at most $1 \times 10^{-5}$ of the amount present prior to treatment, if such bacterium had been present.

*Listeria* pasteurized means subjecting (or having been subjected) to a treatment sufficient to reduce the number of viable *Listeria monocytogenes* on or in a product or surface to at most $1 \times 10^{-5}$ of the amount present prior to treatment, if such bacterium had been present.

*Salmonella* pasteurized means subjecting (or having been subjected) to a treatment sufficient to reduce the number of viable *Salmonella enterica* subsp. *enterica* serovar *enteritidis* on or in a product or surface to at most $1 \times 10^{-5}$ of the amount present prior to treatment, if such bacterium had been present.

The phrase "contains too much mycotoxin for use as human food by US standards" means that the product referenced contains more than 20 parts-per-billion (ppb) aflatoxins, more than 1000 ppb deoxynivalenol, and/or more than 200 ppb fumonisins, while the phrase "is suitable for use as human food by US standards" means that the product referenced contains at most 20 ppb aflatoxins, at most 1000 ppb deoxynivalenol, and at most 200 ppb fumonisins.

The phrase "contains too much mycotoxin for use as human food by EU standards" means that the product referenced contains more than 2 ppb aflatoxin B1, more than 4 ppb total aflatoxins, more than 750 ppb deoxynivalenol, more than 1000 ppb fumonisins and/or more than 75 ppb zearalenone, while the phrase "is suitable for use as human food by EU standards" means that the product referenced contains at most 2 ppb aflatoxin B1, at most 4 ppb total aflatoxins, at most 750 ppb deoxynivalenol, at most 1000 ppb fumonisins and at most 75 ppb zearalenone.

The phrase "contains too much mycotoxin for use as animal feed by US standards" means that the product referenced contains more than 20 ppb aflatoxins, more than 5000 ppb deoxynivalenol, more than 5000 ppb fumonisins and/or more than 1000 ppb zearalenone, while the phrase "is suitable for use as animal feed by US standards" means that the product referenced contains at most 20 ppb aflatoxins, at most 5000 ppb deoxynivalenol, at most 5000 ppb fumonisins and at most 1000 ppb zearalenone.

The phrase "contains too much mycotoxin for use as animal feed by EU standards" means that the product referenced contains more than 10 ppb aflatoxins, more than 1750 ppb deoxynivalenol, more than 4000 ppb fumonisins and/or more than 100 ppb zearalenone, while the phrase "is suitable for use as animal feed by EU standards" means that the product referenced contains at most 10 ppb aflatoxins, at most 1750 ppb deoxynivalenol, at most 4000 ppb fumonisins and at most 100 ppb zearalenone.

BRIEF DESCRIPTION OF THE DRAWINGS

The following figures are provided to help illustrate the products, devices and methods of the application, but other variations and configurations are possible. The figures are not drawn to scale, with the size of some parts increased or decreased for clarity.

DETAILED DESCRIPTION

The present invention makes use of reactive gas produced by HVCP. The reactive gas is able to sterilize or pasteurize surfaces even when transported a significant distance from the DBD system where the plasma is produced, for example 3 to 30 meters (or 10 to 100 feet). Furthermore, the reactive gas is able to break down some organic and biological materials, such as mycotoxins. This is quite surprising, because unlike HVCP produced within a package, there is no direct exposure of the product to the HVCP, the contact time of the reactive gas with the product is limited, for example for 1 second, 1 minute, 30 minutes, or one hour. Furthermore, because the reactive gas is transported away from the DBD system where the HVCP is produced, it is diluted by both diffusion into the surrounding gas, and mixed with the surrounding gas and/or the working gas. Since the reactive gas is transported away from the DBD system, much larger volumes of product may be exposed to the reactive gas, in batch processes or continuous processes. In addition, large scale disinfection, such as disinfection of a surgical suite, may also be carried out.

Figure 1A:
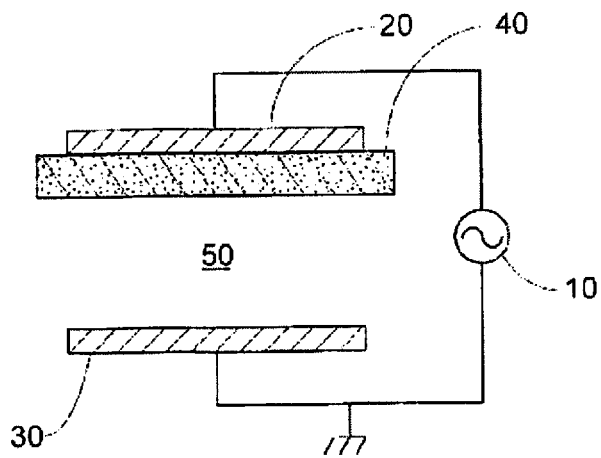
FIGS. 1A, 1B, 1C, 1D, 1E and 1F are schematic illustrations of a variety of DBD systems.
Figure 1B:
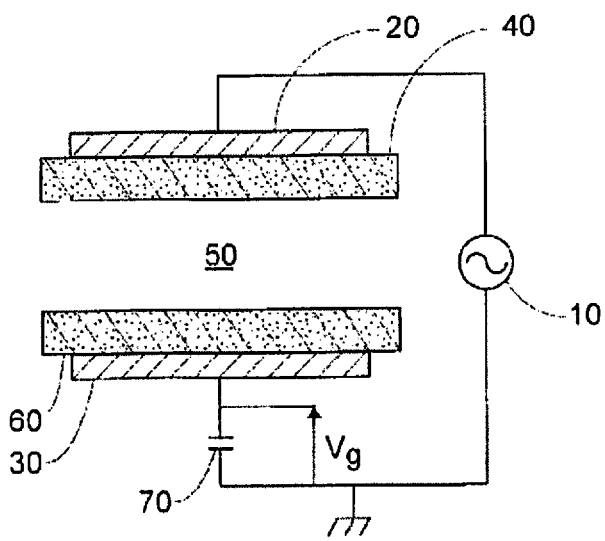
Figure 1C:
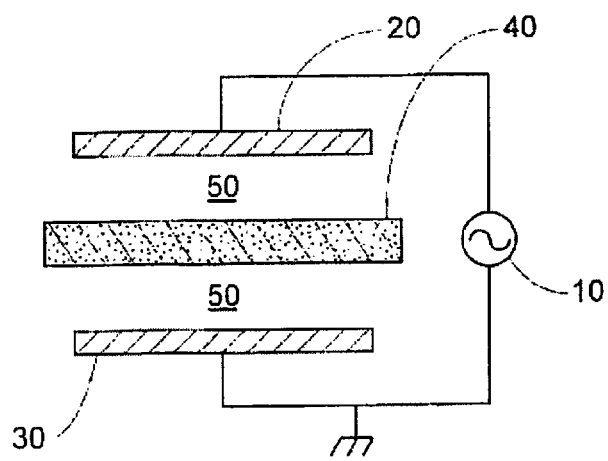
Figure 1D:
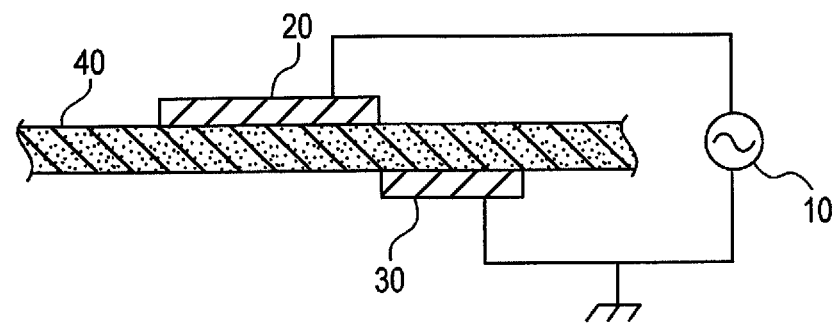
Figure 1E:
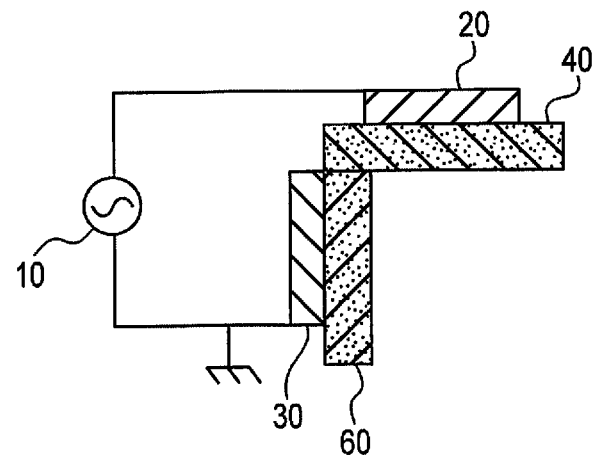
Figure 1F:
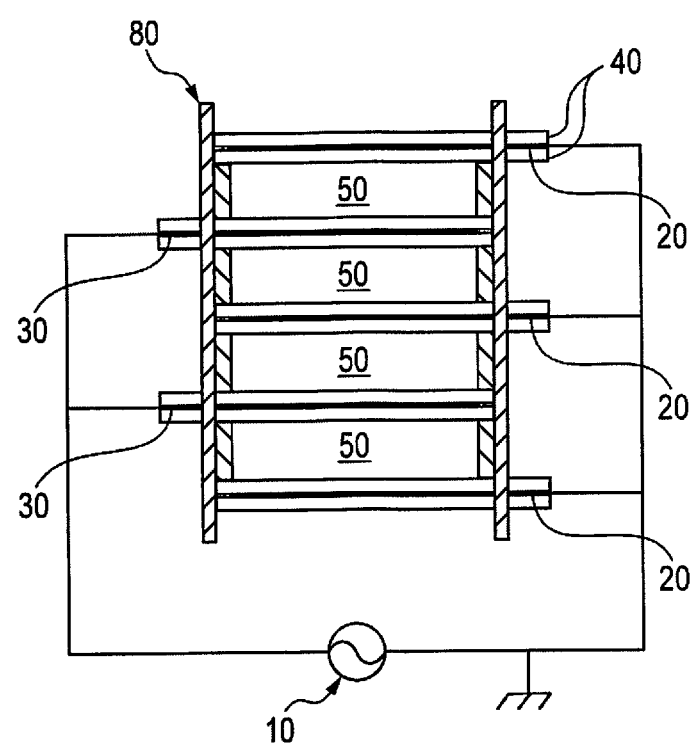

FIGS. 1A, 1B, 1C, 1D, 1E and 1F are schematic illustrations of a variety of DBD systems which may be used to produce HVCP which produces a reactive gas. A DBD system includes a high voltage source, 10, having a ground which generates an alternating current, a first electrode, 20, a second electrode, 30, and an intervening dielectric, 40. One or more additional intervening dielectrics, 60, may also be present between the first and second electrode. In some configurations the dielectric may surround the first and/or second electrode. In some configurations, the charge accumulation on the electrodes, used in conjunction with the voltage waveform, may be used to estimate the power consumption of the DBD system, and may be measured by determining the voltage developed across a conventional capacitor or other sensor, 70. Preferably, a plenum, 50, is present, which defines a space between the electrodes where the HVCP and the reactive gas are produced, as shown in FIGS. 1A, 1B, 1C and 1F. However, the HVCP and reactive gas may also be produced in the vicinity of the dielectrics even when a clear plenum is not present in the DBD system, such as illustrated in FIGS. 1D and 1E. In some configurations, multiple electrodes, such as 3 to 10 electrode, 4 to 8 electrodes, or 5 to 7 electrodes, with one or more intervening dielectrics between each pair of adjacent electrode, and optionally forming multiple plenums, may be used, such as that illustrated in FIG. 1F (where a frame, 80, may be used to hold each electrode-dielectric assembly (such as 40, 20, and 40) to define each plenum (50)); such an arrangement allows for the production of a greater amount of HVCP and therefore production of reactive gas, while maintaining the appropriate distance between electrodes and keeping the system compact. The configuration of the DBD system results in limiting of the current of any filamentary discharge that is formed between the electrodes so as to prevent the formation of a high current arc. In a preferred arrangement, a first electrode is fully enclosed in a dielectric, and a second electrode is grounded.

The electrodes may be formed from any conductive material, such as a metal. The dielectrics may be formed from any insulating material (dielectric material), such as ceramics, glass, organic materials, or plastics, including multiple layers of various compositions. The thickness of the dielectric, or different layers of dielectric, should be selected to limit the current of any filamentary discharge that may form between the electrodes. Selection of materials for the dielectric layers may have an effect on the reactive gas composition.

The distance between adjacent electrodes when the electrodes are parallel, or the shortest distance between adjacent electrodes when the electrode are not parallel, is preferably at most 30 cm (or 12 inches), and preferably is at least 0.5 cm (or 0.25 inches), such as 1 to 10 cm, or 2.5 to 6 cm (or 1 to 2 inches), including 2, 3, 4, 5, 6, 7, 8 and 9 cm. The high voltage source produces a voltage of at most 500 kV, more preferably 30 kV to 150 kV, including 40, 50, 60, 70, 80, 90, 95, 100, 110, 120, 130 and 140 kV; having a frequency of at most 1000 Hz, more preferably 10 to 100 Hz, such as 50 to 60 Hz. Time variant (that is, pulsed) DC power may also be used. Although the frequency is chosen primarily for convenience (for example, 50 or 60 Hz AC power is available from the municipal power grid), voltage is selected to ensure the production of HVCP.

Different selection of working gases and working gas mixtures will affect the species present in the reactive gas produced by the HVCP. Examples of gases which may be used to prepare the HVCP include oxygen ($O_2$); nitrogen ($N_2$); water vapor ($H_2O$); inert and noble gases such as helium (He), neon (Ne), argon (Ar), krypton (Kr), xenon (Xe) and sulfur hexafluoride ($SF_6$); hydrogen ($H_2$); carbon dioxide ($CO_2$) and carbon monoxide (CO); halogens and pseudohalogens such as fluorine ($F_2$), chlorine ($Cl_2$), bromine ($Br_2$), and cyanogen ($(CN)_2$); acidic gases such as hydrogen sulfide ($H_2S$), hydrogen fluoride (HF), hydrogen chloride (HCl), and carbonyl sulfide (COS); ammonia ($NH_3$); hydrazine ($H_4N_2$); nitrogen trifluoride ($NF_3$); chlorine dioxide ($ClO_2$); hydrocarbons such as methane ($CH_4$), ethane ($C_2H_6$) and acetylene ($H_2C_2$); alcohols such as methanol ($CH_3OH$) and ethanol ($C_2H_5OH$); and mixtures thereof. Preferred gases include air and MA65 (a mixture of 65% $O_2$, 30% $CO_2$, and 5% $N_2$). Increasing the amount of water vapor in the gas may be used to reduce ozone present in the reactive gas. Increasing the amount of noble gas, such as helium, may be used to reduce the voltage needed to produce the HVCP. The pressure of the gas use to prepare the HVCP is conveniently selected as ambient or atmospheric pressure, but other pressures may be used, such as 10 to 50000 Torr, more preferably 100 to 1000 Torr, such as 760 Torr (atmospheric pressure).

The reactive gas contains a variety of reactive and excited species, and the reactive gas always contains at least one (and typically more than one) reactive and/or excited species which is not present in the working gas. When the working gas contains oxygen (for example, $O_2$, $CO_2$, and/or $H_2O$) ozone may form; however, the properties and reactions of the reactive gas are not explained by the presence of ozone alone, and the reactive gas always contains other reactive and excited species in addition to any ozone (which may, or may not, be present in the reactive gas). In addition to ozone, other reactive and excited species which may be present in reactive gas include: singlet oxygen ($^1O_2$) and other excited molecular species (both vibrationally excited molecules and electronically excited atoms and/or molecules, such as $O_2$, $H_2$, $N_2$, CO, $CO_2$, $H_2O$, He, Ne, Ar, Kr and Xe), hydroxyl radical (HO*), nitrogen oxides (such as $N_2O$, NO, $NO_2$, $NO_3$, $N_2O_3$, $N_2O_4$ and $N_2O_5$), hydrogen peroxide ($H_2O_2$), hydroperoxyl ($HO_2$), HNOx species (such as $HNO_4$, $HNO_3$ and HNO), atomic radicals (such a O, F, Cl, N and H), and molecular radicals (such as hydrocarbon radicals, which may also contain one or more of oxygen, nitrogen, fluorine and chlorine). Preferably, the reactive gas has at least one additional reactive and/or excited species in addition to ozone and $NO_2$ (or $N_2O_4$) (which may, or may not, be present). Unlike HVCP, reactive gas is not a plasma and does not contain free electrons. Preferably, the reactive gas contains at least 2 different reactive and/or excited species listed above, more preferably at least 3 different reactive and/or excited species listed above, even more preferably at least 4 different reactive and/or excited species listed above, and most preferably at least 5 different reactive and/or excited species listed above, including 2-10 or 3-8 or 4-6 different reactive and/or excited species listed above.

It is also possible to capture and store the reactive gas in a container for later use. Preferably, the stored reactive gas is used to treat a product or surface within 24 hours after it is produced, more preferably within 12 hours, most preferably within 6, even more preferably with 3 hours.

The reactive gas may also be captured and stored by cooling to extremely low temperatures, for example using liquid nitrogen as a coolant, or using liquid helium as a coolant. When captured and stored at such low temperatures, the reactive gas may be stored for extended periods of time, for example 1 day to 6 weeks, and possibly longer. Containers, such a glass or metal containers used to store other liquefied or solidified gases, may be used.

A reactive gas treatment system includes either a DBD system or stored reactive gas, and a treatment chamber. The reactive gas treatment system also includes a device, mechanism, or a configuration for moving the reactive gas away from the DBD system (which produces a HVCP, which in turn produces the reactive gas) or from a container having stored reactive gas, and into or throughout the treatment chamber; this may be a fluid connection between the DBD system and the treatment chamber. Preferably, the treatment chamber is not sealed; such an unsealed chamber would include a treatment chamber with a gas outlet. Preferably, the treatment chamber has a volume of at least 28 liters (or 1 cubic foot), more preferably a volume of at least 1 cubic meter, and even more preferably at least 8 cubic meters. Examples of treatment chambers include rooms, bins, grain dryers, silos, tanks and shipping containers.

The reactive gas system may be used to carry out a method of treating a product and/or a surface, by supplying the reactive gas (either from stored reactive gas, or by generating a HVCP using a DBD system), and distributing the reactive gas into or throughout the treatment chamber.

Examples of a device, mechanism, or configuration for moving the reactive gas includes convection, a gas pathway or gas line, a fan, and supplying flowing or pressurized working gas to the DBD system. Preferably, the product or surface treated by the reactive gas is not heated (that is, its temperature is not increased) by the method of treatment by more than 40° C., more preferably by not more than 20° C., even more preferably by not more than 10° C., and most preferably by not more than 5° C., such as no heating of the product or surface. Treatment with the reactive gas is a non-thermal processing method. Preferably, products or surfaces are not exposed to radiation (such as UV light) produced by a HVCP during the method. Optionally, air, a working gas, or another gas (such as a noble gas or nitrogen) may be used to flush the reactive gas out of the treatment chamber, or the treatment chamber may be evacuated. The method may be optionally repeated 1, 2, 3 or more times, to provide multiple treatments to products or surfaces. Optionally, product may be sealed into a container and/or refrigerated after treatment with a reactive gas. Preferably, the product to be treated is not enclosed in a sealed or substantially sealed contain, such as a container have a volume of at most 10 gallons, or at most 6 gallons, during treatment. Preferably, the HVCP is not produced inside a sealed container, such as a container have a volume of at most 10 gallons, or at most 6 gallons.

The reactive gas produced by the HVCP is transported away from the site of production of the HVCP (to avoid direct exposure of the product or surface to the HVCP), by diffusion or gas transfer. Preferably, the distance between the plasma and the product or surface to be treated is at least a distance of 5 cm, such as at least 10 cm, at least 50 cm, and at least 1 meter (or 3.28 feet), more preferably at least 3 meters, for example 3 to 300 meters, including 5, 10, 20, 30, 40 and 50 meters. In most configurations, the reactive gas is allowed to flow while it is in contact with a product or surface to be treated, although it is also possible to produce the reactive gas and transfer it to a site to treat the product or surface, and confine the gas to the treatment location for a period of time. Examples of flow rates for transferring the reactive gas to a location for contact with a product or surface include 10 to 3000 meters/minute, 30 to 2500 meters per minute, and 1000 to 2000 meters/minute, such as 50, 100, 200, 300, 400, 500, 750, and 1500 meters/minute. The reactive gas is allowed to contact the product or surface for at least 1 second, for example at least 2 seconds, at least 10 seconds, at least 30 seconds, at least 1 minute, at least 10 minutes, at least 30 minutes, at least 35 minutes, at least 1 hour, at least 6 hours, or at least 12 hours. Examples of contact times include 1 second to 12 hours, 10 seconds to 1 hour, 1 minute to 35 minutes, including 5 seconds, 15 seconds, 2 minutes, 5 minutes, 20 minutes, 35 minutes, 40 minutes, 2 hours, 3 hours, 4 hours and 5 hours.

Figure 2:
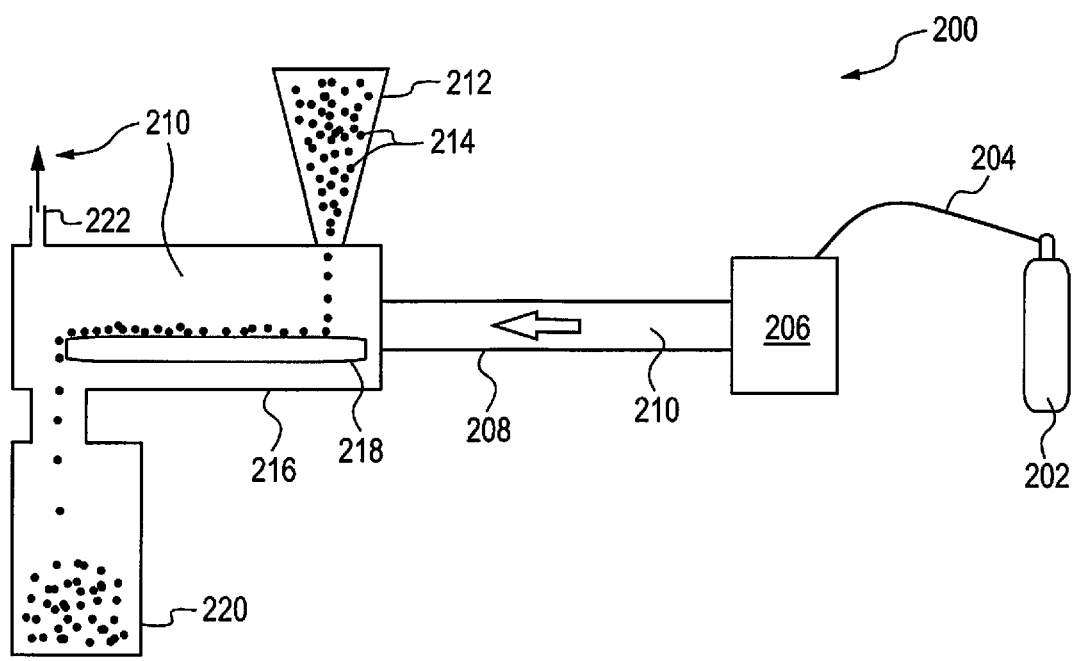
FIG. 2 is a schematic illustration of a reactive gas treatment system for continuous treatment of a product or a surface with a reactive gas.

FIG. 2 is a schematic illustration of a reactive gas treatment system, 200, for continuous treatment of a product or a surface with a reactive gas. The system includes a DBD system, 206, for generating a HVCP to produce a reactive gas, 210. The reactive gas flows along a gas pathway, 208, into a treatment chamber, 216, and then out a gas outlet, 222. Product, 214, to be treated or which has a surface to be treated, may be stored in a hopper, 212, as it is fed into the treatment chamber, and onto a conveyor, 218, which moves the product through the treatment chamber and into a receiving bin, 220, for hold the product after it has been contacted with the reactive gas. Also illustrated is a gas source, 202, such as a gas tank, which provides a working gas from which the HVCP is formed, and a gas line, 204, which supplied the DBD system with the working gas. The reactive gas may be diluted with additional working gas as it flows through the system. The transport of the reactive gas from the DBD system to the treatment chamber is by way of a pressure differential between the DBD system (at higher pressure from introduction of the working gas) and the treatment chamber (at lower pressure due to the gas outlet). Optionally, the gas outlet may be connected back to the DBD system by a second gas line, allowing for recycling of the working gas and any remaining reactive gas. Optionally, the DBD system may be located inside the treatment chamber, avoiding the need for a gas pathway. In a variation, the working gas may be air, and the transport of the reactive gas may be caused by a fan located in the gas pathway (blowing the reactive gas into the treatment chamber) or at the back of the DBD system (blowing air through the DBD system). Optionally, the conveyor may transport the product on a screen to ensure that the reactive gas comes into contact on all surfaces of the product. Furthermore, product may be moved through the treatment chamber on a plurality of conveyors, where the product is shifted around as it moves from a first conveyor to a second conveyor, ensuring that the reactive gas comes into contact with all surfaces of the product. In another variation, the DBD system may be eliminated, by using a stored reactive gas as the gas source and transporting the reactive gas directly to the treatment chamber. A variety of different conveyors may be used, such as a permeable belt conveyor, a screw, a tunnel dryer, a grain dryer or a cylindrical dryer.

Figure 3:
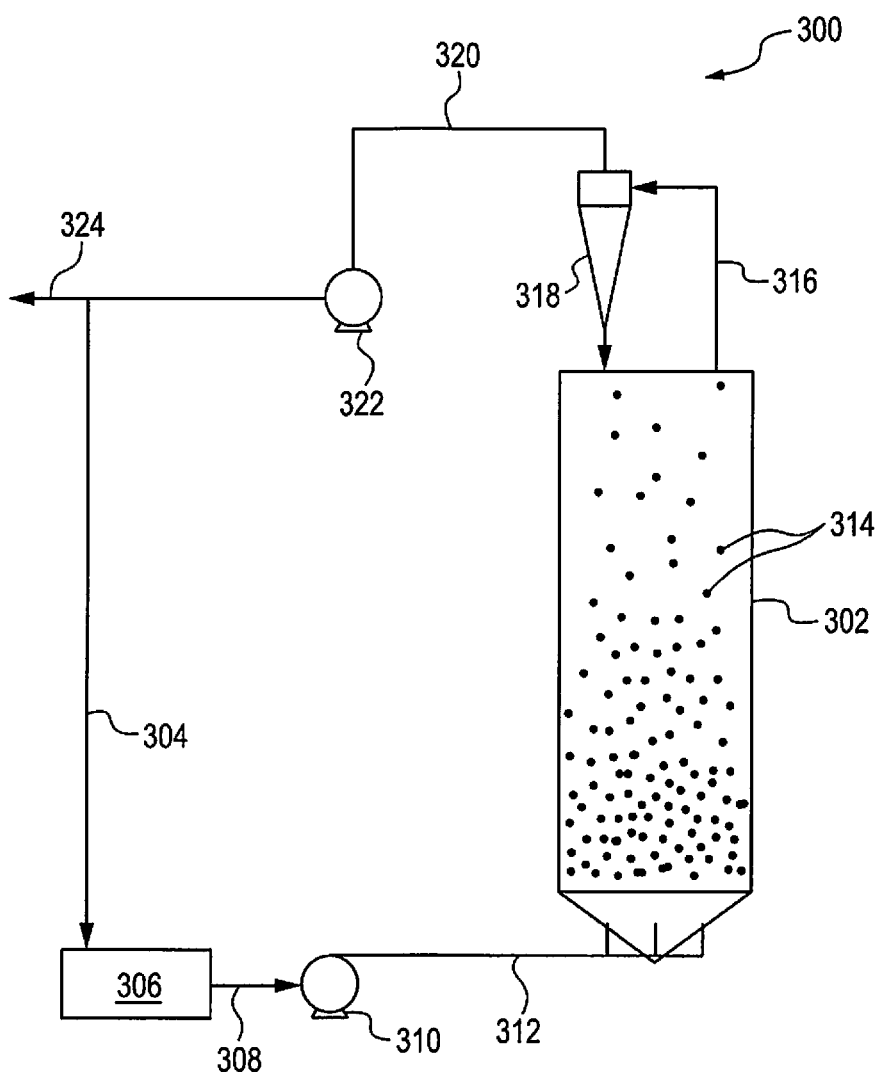
FIG. 3 is a schematic illustration of a reactive gas treatment system for batch treatment of a product or a surface with a reactive gas.

FIG. 3 is a schematic illustration of a reactive gas treatment system, 300, for batch treatment of a product or a surface with a reactive gas. The system includes a DBD system, 306, for generating a HVCP to produce a reactive gas. The reactive gas flows along gas pathways, 308 and 312, into a treatment chamber, 302, and then out through a gas pathway, 316, through an optional product recovery trap, 318, along a gas pathway, 320, and out through a gas outlet, 324. Some or all of the reactive gas and working gas may be recycled back to the DBD system through an optional gas pathway, 304. The reactive gas and working gas is propelled through the system by fans, 310 and 322. Product, 314, to be treated or which has a surface to be treated, is present in the treatment chamber; as illustrated the reactive gas is fed in through the bottom of the treatment chamber to create a fluidized bed from of the reactive gas and the product to ensure treatment of all surfaces of the product. The product recovery trap may be used to capture any product which exits the treatment chamber and into the gas pathway, and return it back to the treatment chamber. The treatment chamber may be a silo in the system illustrated; other treatment chambers include a fluid bed, a mechanical fluid bed, and a bin. The reactive gas may be diluted with addition working gas as it flows through the system. As illustrated, the working gas may be air, but optionally the gas pathway, 304, may be connected to a gas source for supplying a working gas to the DBD system. In another variation, the DBD system may be eliminated and replaced with stored reactive gas.

Any product or surface may be treated with the reactive gas, to sterilize (medical sterilization or canning sterilization) or pasteurize (*Salmonella* pasteurized, *Listeria* pasteurized or *E. coli* pasteurized) the product or its surface, and/or removed contaminates, such as toxins. Examples of products includes fresh foods (such as fruits, vegetables, grains, beans, seeds, meat, dairy products, eggs, and spices or seasonings), seafood (fish and shell fish, and their parts), prepared foods, frozen foods, processed foods prior to packaging (water, beverages, baby food, liquid eggs, fruit juice, flour, oil, nutritional product, vitamins, nutraceuticals and baked foods), packaged products (for treatment of the exterior of the packages), animal feed, cans, bottles, plastic containers, food containers, cookware and utensils; pills, capsules, unit dosage forms and powders; medical devices and medical equipment, both before use and after use; laboratory glass and plastic ware; ceramic products; metal products; and leather and wood products.

If a sufficient reduction in viable microorganisms (or microorganism spores) is not accomplished by treatment with the reactive gas, successive treatments may be conducted until the desired reduction is achieved, for example sufficient to achieve medical sterilization or canning sterilization. For example, 1 to 10 treatments may be carried out, or 2 to 9 treatments, including 3, 4, 5, 6, 7 or 8 treatments may be carried out. Similarly, the time of treatment may also be extended. Preferably, treatment with reactive gas is repeated until medical sterilization or canning sterilization is achieved, or *Salmonella* pasteurization, *Listeria* pasteurization or *E. coli* pasteurization is achieved.

As with sterilization or pasteurization, if a sufficient reduction in toxin (such as mycotoxin or aflatoxin) is not accomplished by treatment with the reactive gas, successive treatments may be conducted until the desired reduction is achieved. For example, the treatment may be repeated until a reduction is achieved of at least a 50% reduction, at least a 90% reduction, a reduction to at most a $1\times10^{-1}$ of the amount present prior to treatment, a reduction to at most $1\times10^{-2}$ of the amount present prior to treatment, or even a reduction to at most $1\times10^{-3}$ of the amount present prior to treatment.

Surfaces of products, rooms and container may be treated with reactive gas, to deodorize, remove pests and insects, remove or kill mold, sterilize, pasteurize, bleaching, and destroy toxins such as biological toxins and pesticides. The reactive gas may also be used to treat waste water, exhaust gases (such as automobile exhaust), chemically modify oils, and denature enzymes.

Fruits (such as fruit parts and dried fruit), and seeds (for example seed parts; grains such as wheat, rice and corn; legumes such as peas, beans, lentils, soybeans and peanuts; and nuts such as cashews, macadamia nuts, hazelnuts, chestnuts, acorns, almonds, pecans, pistachios, walnuts and Brazil nuts), in particular those contaminated with mycotoxins, such as aflatoxins, are preferred products because the reactive gas is able to destroy such toxins, making such products that were previously unsuitable for human or animal consumption, usable for such purposes. Examples of toxins which may be eliminated or reduced with contact with reactive gas include: aflatoxin (such as aflatoxin B1, B2, G1 and G2), deoxynivalenol (such as 15-acetyl deoxynivalenol and 3-acetyl deoxynivalenol), ochratoxin A, T2 toxin, HT-2 toxin, zearalenone and fumonisin (such as fumonisin B1, B2 and B3). The table below indicates the amount of various mycotoxins above which a product is not suitable for use as human food or animal feed, both in the US and Europe (EU). Reactive gas treatment, including repeated reactive gas treatment may be use to remove sufficient mycotoxins to transform a product which is not suitable for use as human food or animal feed into a product which is suitable for use as human food or animal feed.

TABLE 1

Recommendations and regulations for safe limits on mycotoxin concentrations in grain in the United States and European Union, as of 2008.

| Mycotoxin | Grain for human food | | Grain for animal feed | |
|---|---|---|---|---|
| | USA[a] | EU[b] | USA[a] | EU[b] |
| Aflatoxins | 20 ppb | 2-4 ppb[c] | 20-300 ppb[d] | 10-50 ppb[d] |
| Deoxynivalenol | 1000 ppb | 750 ppb | 5,000-10,000 ppb[d] | 1,750 ppb |
| Fumonisins | 200-4,000 ppb[c] | 1,000 ppb | 5,000-100,000 ppb[d] | 4,000 ppb |
| Zearalenone | No guidance levels; case-bycase basis | 75-100 ppb[c] | 1,000-200,000 ppb[d] | 100-350 ppb[d] |

Figure 4:
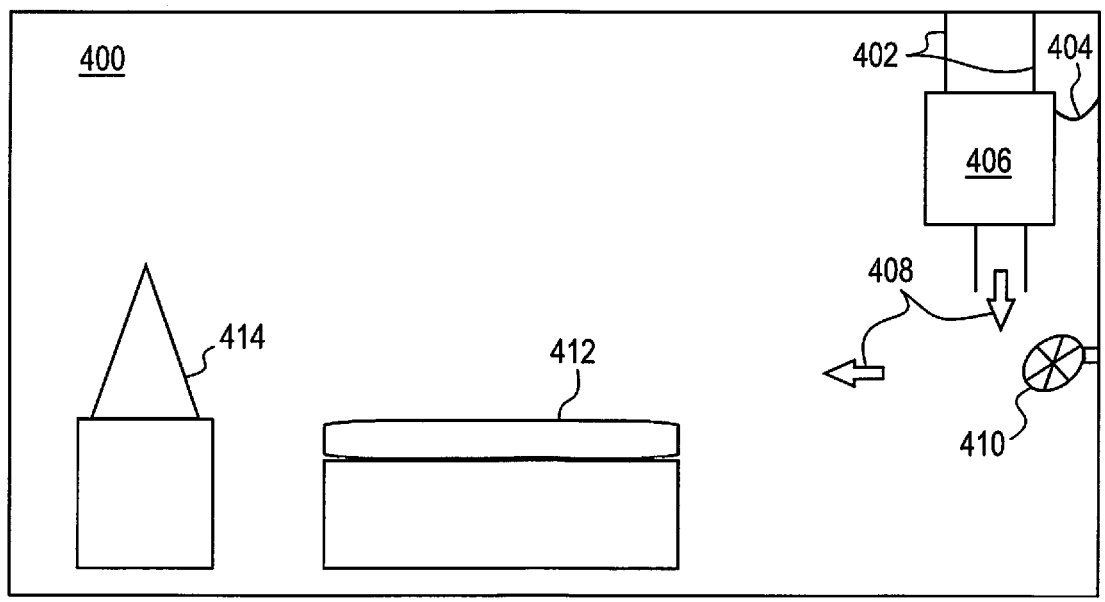
FIG. 4 is a schematic illustration of a reactive gas treatment system for treatment of equipment and/or surfaces with an enclosed space

[a]Munkvold, 2003a
[b]Commission Regulation (EC) No 1126/2007
[c]Varies among specific food items
[d]Varies among livestock species FIG. 4 is a schematic illustration of a reactive gas treatment system for treatment of equipment and/or surfaces with an enclosed space, such as a room, a shipping container, a trailer or a refrigerated truck. Within the treatment chamber, 400, which here is the enclosed space, is a DBD system, 406, for generating a HVCP to produce a reactive gas, 408. A fan, 410, is used to distribute the reactive gas throughout the enclosed space. Also illustrated are product or surfaces to be treated, which includes the walls or interior surfaces of the enclosed space, optional equipment, 414, such a medical equipment (for example, surgical instruments, masks, assisted breathing equipment, and vital signs monitors), and/or optional surfaces, 412, such as a surgical table, to be treated with the reactive gas. Optionally, supports, 402, could be used to mount the DBD system to the top or the sides of the enclosed space, or the DBD system could be place on the floor of the enclosed space. Optionally, a working gas supply could be supplied by a gas line, 404, connected to a gas supply (not illustrated). Alternatively, the enclosed space could be filled with a working gas. In another configuration, the DBD system could be replaced with stored reactive gas.

EXAMPLES

The following examples are test systems to show the effects and properties of reactive gas, where a HVCP was used to produce the reactive gas. In a typical system, the scale would be increased to achieve treatment of commercially significant amounts of product. All HVCP was produced using power at 60 Hz.

Example 1: Treating Whole Corn to Reduce Microbial Load Simulating Short Duration Reactive Gas Exposure 100 g of whole corn was place in an ArtBin® Polypropylene (PP) Container (model 9100AB)—size 37.0 cm×35.5 cm×5.2 cm (L×W×H). The ArtBin® was place inside a second bag composed of Cryovac® B2630 high barrier film—size 40.0 cm×47.0 cm (L×W). Each bag was flushed for 3 minutes (37 L/min.) with MA65 (65% $O_2$, 30% $CO_2$, 5% $N_2$) as fill gas and then sealed. The bag was then placed within a DBD system, between two-4 electrode sets (each electrode: aluminum, 15.24 cm diameter, 8 electrodes total—4 top, 4 bottom) to produce a HVCP within the bag, but not in contact with the whole corn in the ArtBin®. Treatment times were 5 minutes and 15 minutes for the whole corn samples with 280-290 watts power consumption.

The height (gap) was 5.2 cm between the electrodes. The HVCP were formed at 95 kV with an amperage of 1.0-1.5 mA. The dielectric barriers were used to regulate plasma field characteristics inside the bags: (1) cutting boards (IKEA® brand, 37 cm×29 cm×2 cm); (2) plexiglass barrier positioned on top electrode set; and (3) tote lids (Bella™ brand) from 114 L and/or 151 L totes (two above and one below each bag) for additional surface area extension of barrier capacity. These dielectric barriers allowed for optimal reactive gas generation from the HVCP.

Ozone and nitrogen oxides were measured by means of Drager® Short-Term Detector tubes (Draeger Safety AG & Co. KGaA, Luebeck, Germany). Immediately after the treatment was complete, the bags were opened and the samples were flushed with fresh gas to remove any remaining reactive gas with the exception of one sample that was treated for 5 minutes and the reactive gas was allowed to remain in the sealed bag for 24 hours before opening.

Total aerobic bacteria colony forming units (CFU/g) were determined by standard spread plate methodology using tryptic soy agar for aerobic bacteria (TSA, Difco brand, Becton, Dickinson and Company (BD), Sparks, Md.). Standard TSA plates for aerobic recoveries were incubated at 37° C. for 24 hours. After 24 hours post reactive gas treatment and storage at room temperature (22° C.), microbial populations were recovered from respective food product(s) using a sterile rinse (0.1% peptone) by agitation for 1 minute in sterile filter stomacher bags to remove microorganisms from product surfaces. Rinse by agitation (hand shaking and vortexing) allowed for external recoveries only, without potential for additional bactericidal interference that may be introduced from internal flesh as a result of stomaching. Recoveries from diluents were obtained by performing serial dilutions and plate enumeration. Microbial colonies were enumerated after the plates were incubated at 37° C. for 24 hours. All microbiological methods were performed according to the U.S. Food and Drug Administration, Bacteriological Analytical Manual (BAM: Bacteriological Analytical Manual, 8th Edition, Final Revision: Jan. 25, 2001). Samples of the whole corn were collected from the same whole corn sample by subdividing the sample and analyzing the samples before and after treatment to obtain the differential reduction in microbial load on the corn.

The table below summarizes the results from this experiment. "Temp." in the table refers to the temperature of the electrodes. Additional reduction, using successive treatments, could be used to achieve as great a reduction as desired.

TABLE 1

HVCP Process Parameters: 95 kV multi-electrode set up, MA65 gas type, 100 g sample quantity whole corn kernels

| Time (min) | Storage (h) | Experiment | Temp. (° C.) | Log 10 reduction/g | Ozone (ppm) | NOx (ppm) |
|---|---|---|---|---|---|---|
| 5 | 0 | 1 | 32 | 0.35 | 15000 | 1000 |
|   |   | 2 | 33 | 0.35 | 15000 | 2000 |
| Average |   |   |   | 0.35 ± 0.0 | 15000 ± 0.0 | 1500 ± 707 |
| 5 | 24 | 1 | 35 | 1.12 | 15000 | 1000 |
|   |   | 2 | 34 | 1.66 | 17500 | 1500 |
|   |   | 3 | 38 | 1.43 | 8000? | 1600 |
|   |   | 4 | 38 | 1.36 | 15000 | 2000 |
| Average |   |   |   | 1.69 ± 0.26 | 15833 ± 1443 | 1525 ± 411.3 |
| 15 | 0 | 1 | 48 | 3.05 | 15000 | 1000 |
|   |   | 2 | 35 | 1.56 | 10000 | 2000 |
|   |   | 3 | 38 | 1.75 | 8000 | 1200 |
| Average |   |   |   | 2.25 ± 0.34 | 11000 ± 3535 | 1333 ± 707 |

Example 2: Treating Whole Wheat to Reduce Microbial Load Simulating Short Reactive Gas Exposure 100 g of whole wheat was instead of whole corn, and the experiments and measurement carried out in Example 1 were repeated. The table below summarizes the results from this experiment. "Temp." in the table refers to the temperature of the electrodes. Additional reduction, using successive treatments, could be used to achieve as great a reduction as desired.

TABLE 2

HVCP Process Parameters: 95 kV multi-electrode set up, MA65 gas type, 100 g sample of whole wheat kernels

| Time (min) | Storage (h) | Experiment | Temp. (° C.) | Log10 reduction/g | Ozone (ppm) | NOx (ppm) |
|---|---|---|---|---|---|---|
| 5 | 0 | 1 | 38 | 0 | 9250 | 4000 |
|   |   | 2 | 41 | 0 | 17500 | 6000 |
| Average |   |   |   | 0 | 13375 ± 5833 | 5000 ± 1414 |
| 5 | 24 | 1 | 33 | 0.79 | 7500 | 1000 |
|   |   | 2 | 37 | 1.23 | 10000 | 1500 |
| Average |   |   |   | 1.01 ± 0.31 | 8750 ± 1767 | 1250 ± 353 |

TABLE 2-continued

| | | | | HVCP Process Parameters: 95 kV multi-electrode set up, MA65 gas type, 100 g sample of whole wheat kernels | | |
|---|---|---|---|---|---|---|
| Time (min) | Storage (h) | Experiment | Temp. (° C.) | Log10 reduction/g | Ozone (ppm) | NOx (ppm) |
| 15 | 0 | 1 | 48 | 0.46 | 7000 | 500 |
| | | 2 | 53 | 0.62 | 5500 | 800 |
| Average | | | | 0.54 ± 0.11 | 6250 ± 1060 | 650 ± 212 |

Example 3: Treatment of a Known Reference Sample Containing Mycotoxins to Show a Reduction 50 grams of a naturally contaminated multi-toxin corn product supplied by Trilogy Analytical Laboratory, Washington, Mo. (Trilogy® Reference Material, Product #: TR-MT500, Batch #: MTC-9999E) with known concentrations of mycotoxins was place in an ArtBin® Polypropylene (PP) Container (model 9100AB)—size 37.0 cm×35.5 cm×5.2 cm (L×W×H). The ArtBin® was place inside a second bag composed of Cryovac® B2630 high barrier film—size 40.0 cm×47.0 cm (L×W). Each bag was flushed for 3 minutes (37 L/min) with either Air (22% $O_2$, 78% $N_2$) or MA65 (65% $O_2$, 30% $CO_2$, 5% $N_2$) as fill gas and then sealed. Humidification of the gas used in some of the experiments was performed using a bubble (resulting in about 60% humidity). The bag was then placed within a DBD system, between two-4 electrode sets (each electrode: aluminum, 15.24 cm diameter, 8 electrodes total—4 top, 4 bottom) to produce a HVCP within the bag, but not in contact with the product in the ArtBin®. The HVCP was formed at 100 kV with an amperage of 0.6-1.8 mA across all samples. The dielectric barriers were used to regulate plasma field characteristics inside the bags: (1) cutting boards (IKEA® brand, 37 cm×29 cm×2 cm); (2) plexiglass barrier positioned on top electrode set; and (3) tote lids (Bella™ brand) from 114 L and/or 151 L totes (two above and one below each bag) for additional surface area extension of barrier capacity. All product samples were treated for treatment times of 30 min and then stored for 24 hours post treatment under room temperature (22° C.) conditions. After 24 hours storage, all test samples and controls were sent to Trilogy Analytical Laboratory, Washington, MO for a complete mycotoxin panel (#6).

The following two tables show the result from these experiments. In the table. "ND" means "not detected." In Table 3, the total toxin in the reference was 40.67 ppm, while after treatment the total was only 13.00 ppm, resulting in a total reduction of 68%. In Table 4, the total toxin in the reference was 45.97 ppm, while after treatment the total was only 23.75 ppm, resulting in a total reduction of 48%. Additional reduction, using successive treatments, could be used to achieve as great a reduction as desired.

TABLE 3

Mycotoxin reduction results using MA65 working gas and 100 kV for 30 minutes

| | | Dry MA65 | | Humidified MA65 | | % |
|---|---|---|---|---|---|---|
| Toxin | Reference | A-1 | A-2 | A-3 | A-4 | Reduction |
| Aflatoxin B1 | 18.8 ppb | 7.3 ppb | 7.4 ppb | 8.2 ppb | 7.4 ppb | 61% |
| Aflatoxin B2 | 0.9 ppb | ND | ND | ND | ND | 100% |
| Aflatoxin G1 | 2.4 ppb | ND | ND | ND | ND | 100% |
| Aflatoxin G2 | ND | ND | ND | ND | ND | |
| Deoxynivalenol | 2.6 ppm | 1.5 ppm | 1.5 ppm | 1.6 ppm | 1.4 ppm | 42% |
| 15-Acetyl Deoxynivalenol | | 0.2 ppm | 0.1 ppm | 0.2 ppm | ND | |
| 3-Acetyl Deoxynivalenol | | ND | ND | ND | ND | |
| Ochratoxin A | 4 ppb | 2.7 ppb | 1.9 ppb | 2.7 ppb | 2.4 ppb | 40% |
| T2 Toxin | 263.7 ppb | 228 ppb | 242 ppb | 245 ppb | 266 ppb | 0% |
| HT-2 Toxin | 523.3 ppb | 521 ppb | 522 ppb | 530 ppb | 525 ppb | 0% |
| Zearalenone | 352.0 ppb | ND | ND | ND | ND | 100% |
| Fumonisin B1 | 28.1 ppm | 8.3 ppm | 8.1 ppm | 7 ppm | 7.3 ppm | 72% |
| Fumonisin B2 | 7.1 ppm | 2 ppm | 1.9 ppm | 1.8 ppm | 1.9 ppm | 73% |
| Fumonisin B3 | 1.7 ppm | 0.9 ppm | 1 ppm | 0.8 ppm | 0.8 ppm | 53% |

TABLE 4

Mycotoxin reduction results using air working gas at 100 kV for 30 minutes

| | | Dry Air | | % |
|---|---|---|---|---|
| Toxin | Reference | TA-1 | TA-2 | Reduction |
| Aflatoxin B1 | 18.9 ppb | 14.9 ppb | 16.5 ppb | 16% |
| Aflatoxin B2 | ND | ND | ND | |
| Aflatoxin G1 | ND | ND | ND | |
| Aflatoxin G2 | ND | ND | ND | |
| Deoxynivalenol | 2.3 ppm | 2.4 ppm | 2.2 ppm | 0% |
| 15-Acetyl Deoxynivalenol | 0.3 ppm | 0.2 ppm | 0.2 ppm | |
| 3-Acetyl Deoxynivalenol | ND | ND | ND | |
| Ochratoxin A | 3.4 ppb | 4 ppb | 3.6 ppb | −12% |
| T2 Toxin | 353.1 ppb | 336.9 ppb | 313.4 ppb | 8% |
| HT-2 Toxin | 561.4 ppb | 505.7 ppb | 512.4 ppb | 10% |
| Zearalenone | 228.6 ppb | 139.7 ppb | 177.6 ppb | 34% |
| Fumonisin B1 | 28.6 ppm | 14.7 ppm | 14.1 ppm | 50% |

TABLE 4-continued

Mycotoxin reduction results using air working gas at 100 kV for 30 minutes

| Toxin | Reference | Dry Air TA-1 | Dry Air TA-2 | % Reduction |
|---|---|---|---|---|
| Fumonisin B2 | 10.8 ppm | 4.9 ppm | 4.6 ppm | 56% |
| Fumonisin B3 | 3 ppm | 1.5 ppm | 1.2 ppm | 55% |

Example 4: Generation and Transport of Reactive Gas

A ¼" diameter polypropylene tube with a ⅛" inner diameter was fitted with two, 20 gauge insulated wires, 180 degrees apart from each other. The wires were five feet in overall length. One foot of each wire were attached to the polypropylene tube using a polyvinylchloride shrink tubing. The apparatus was placed in a stand with two vertical supports to suspend it off the ground. The tubing was connected to a compressed gas tank which had a rotameter to measure the flow of gas that was being passed through the tube. A valve and sampling valve were installed on the discharge of this DBD system to measure the amount of ozone that was being generated as a surrogate for other reactive and excited species that were being generated in addition to ozone. The amount of ozone generated was measured by means of Draeger@ Short-Term Detector tubes (Draeger Safety AG & Co. KGaA, Luebeck, Germany). The working gas used in this experiment was compressed air. Two different flow rates were used to determine if flow rate would affect the reactive and excited species generation rate. Gas flow rates were measure using the rotometer and also measured by the time required to fill a 100 ml syringe which was attached to the sampling valve. Three different measurements were taking over a 30 minute period to determine the average ozone generation rate. The conditions for generating the HVCP were the same for both experiments (30 kV) using 7 watts of power. The table below summarizes the results from this experiment.

TABLE 5

Generation and transport of reactive gas

| | Gas Flow Rate Rotometer (ft/sec) | Gas Flow Rate Syringe (ft/sec) | Calculated residence time in plasma generator (sec) | Ozone (PPM) |
|---|---|---|---|---|
| Run 1 | 1.95 | 2.75 | 0.364 | 8 |
| Run 2 | 4.0 | 4.59 | 0.218 | 8 |

What is claimed is:

1. A method of treating food with a reactive gas, comprising:
producing the reactive gas by forming a high-voltage cold plasma (HVCP) from a working gas;
transporting the reactive gas at least 3 meters away from the HVCP; followed by
contacting the food with the reactive gas;
wherein the HVCP does not contact the food,
the food is *Salmonella, Listeria*, and/or *E. coli* pasteurized by the contacting, and the reactive gas is gas produced by the HVCP.

2. The method of claim 1, wherein the food is not sealed or substantially sealed inside a package during the contacting.

3. The method of claim 1, wherein the food comprises grain.

4. The method of claim 1, further comprising removing the reactive gas from contact with the food, after 1 second to 12 hours.

5. The method of claim 1, wherein the reactive gas comprises ozone and at least one nitrogen oxide.

6. The method of claim 1, wherein the working gas comprises MA65.

7. A method of treating animal feed with a reactive gas, comprising:
producing the reactive gas by forming a high-voltage cold plasma (HVCP) from a working gas;
transporting the reactive gas at least 3 meters away from the HVCP; followed by
contacting the animal feed with the reactive gas;
wherein the HVCP does not contact the animal feed,
the animal feed is *Salmonella, Listeria*, and/or *E. roll* pasteurized by the contacting, and
the reactive gas is gas produced by the HVCP.

8. The method of claim 7, further comprising removing the reactive gas from contact with the animal feed, after 1 second to 12 hours.

9. The method of claim 7, wherein the working gas comprises MA65.

10. The method of claim 7, wherein the reactive gas comprises ozone and at least one nitrogen oxide.

11. The method of claim 1, wherein the food is canning sterilized by the contacting.

12. The method of claim 1, wherein the contacting is carried out with the food in a fluidized bed.

13. The method of claim 1, further comprising removing the reactive gas from contact with the food, after 35 minutes to 12 hours.

14. The method of claim 1, wherein the contacting is carried out with the food moving on a conveyor.

15. The method of claim 1, wherein the contacting is carried out in a treatment chamber having a volume of at least 1 cubic meter.

16. The method of claim 1, wherein the food is *Salmonella* pasteurized by the contacting.

17. The method of claim 1, wherein the food is *Listeria* pasteurized by the contacting.

18. The method of claim 1, wherein the food is *E. coli* pasteurized by the contacting.

19. The method of claim 7, wherein the animal feed is canning sterilized by the contacting.

20. The method of claim 7, wherein the contacting is carried out with the animal feed in a fluidized bed.

21. The Method of claim 7, further comprising removing the reactive gas from contact with the animal feed, after 35 minutes to 12 hours.

22. The method of claim 7, wherein the contacting is carried out with the animal feed moving on a conveyor.

23. The method of claim 7, wherein the contacting is carried out in a treatment chamber having a volume of at least 1 cubic meter.

24. The method of claim 7 wherein the animal feed is *Salmonella* pasteurized by the contacting.

25. The method of claim 7, wherein the animal feed is *Listeria* pasteurized by the contacting.

26. The method of claim 7, wherein the ea mal feed is *E. coli* pasteurized by the contacting.

27. A method of treating fruit or seeds with a reactive gas, comprising:
    producing the reactive gas by forming a high-voltage cold plasma (HVCP) from a working gas;
    transporting the reactive gas at least 3 meters away from the HVCP; followed by
    contacting the fruit or seeds with the reactive gas;
    wherein the HVCP does not contact the fruit or seeds,
    the fruit or seeds is *Salmonella Listeria*, and/or *E. Coli* pasteurized by the contacting, and
    the reactive gas is gas produced by the HVCP.

28. The method of claim 27, wherein the fruit or seeds are canning sterilized by the contacting.

29. The method of claim 27, wherein the working gas comprises MA65.

30. The method of claim 27, wherein the reactive gas comprises ozone and at least one nitrogen oxide.

31. The method of claim 27, wherein the fruit or seeds are whole corn or whole wheat.

32. The method of claim 27, wherein the contacting is carried out with the fruit or seeds in a fluidized bed.

33. The method of claim 27, further comprising removing the reactive gas from contact with the fruit or seeds, after 35 minutes to 12 hours.

34. The method of claim 27, wherein the contacting is carried out with the fruit or seeds moving on a conveyor.

35. The method of claim 27, wherein the contacting is carried out in a treatment chamber having a volume of at least 1 cubic meter.

36. The method of claim 32, wherein the fruit or seeds are canning sterilized by the contacting.

37. The method of claim 27, wherein the fruit or seeds are *Salmonella* pasteurized by the contacting.

38. The method of claim 27, wherein the fruit or seeds are *Listeria* pasteurized by the contacting.

39. The method of claim 27, wherein the fruit or seeds are *E. coli* pasteurized by the contacting.

40. The method of claim 27, wherein the fruit or seeds are human food.

* * * * *

UNITED STATES PATENT AND TRADEMARK OFFICE
CERTIFICATE OF CORRECTION

PATENT NO. : 11,000,045 B2  
APPLICATION NO. : 16/215187  
DATED : May 11, 2021  
INVENTOR(S) : Kevin M. Keener et al.

Page 1 of 1

It is certified that error appears in the above-identified patent and that said Letters Patent is hereby corrected as shown below:

On the Title Page

Item (56) Other Publications:  
Page 3, Column 2, Line 17, please delete "McDonougha," and insert --McDonough,--

In the Claims

Column 16, Line 21, please delete "E. roll" and insert --*E. Coli*--  
Column 16, Line 53, please delete "Method" and insert --method--  
Column 16, Line 65, please delete "ea mal" and insert --animal--  
Column 17, Line 9, please delete "*Salmonella*" and insert --*Salmonella,*--

Signed and Sealed this  
Thirteenth Day of July, 2021

Drew Hirshfeld  
*Performing the Functions and Duties of the  
Under Secretary of Commerce for Intellectual Property and  
Director of the United States Patent and Trademark Office*